United States Patent
Nakano et al.

(10) Patent No.: US 9,925,129 B2
(45) Date of Patent: Mar. 27, 2018

(54) OIL-IN-WATER EMULSION COSMETIC AND METHOD FOR PRODUCING SAME

(71) Applicant: JO COSMETICS CO., LTD., Ota-ku, Tokyo (JP)

(72) Inventors: Akihiro Nakano, Tokyo (JP); Yuichi Kanaya, Tokyo (JP)

(73) Assignee: JO Cosmetics Co., Ltd., Ota-ku, Tokyo (JP)

( * ) Notice: Subject to any disclaimer, the term of this patent is extended or adjusted under 35 U.S.C. 154(b) by 0 days.

(21) Appl. No.: 14/888,888

(22) PCT Filed: May 8, 2014

(86) PCT No.: PCT/JP2014/062297
§ 371 (c)(1),
(2) Date: Nov. 3, 2015

(87) PCT Pub. No.: WO2014/185320
PCT Pub. Date: Nov. 20, 2014

(65) Prior Publication Data
US 2016/0081891 A1    Mar. 24, 2016

(30) Foreign Application Priority Data

May 13, 2013   (JP) ................. 2013-101021

(51) Int. Cl.
| | |
|---|---|
| A61K 8/06 | (2006.01) |
| A61Q 17/04 | (2006.01) |
| A61Q 1/02 | (2006.01) |
| A61K 8/81 | (2006.01) |
| A61K 8/34 | (2006.01) |
| A61K 8/36 | (2006.01) |
| A61Q 19/00 | (2006.01) |
| A61Q 1/00 | (2006.01) |
| A61Q 5/00 | (2006.01) |

(52) U.S. Cl.
CPC ........... *A61K 8/062* (2013.01); *A61K 8/345* (2013.01); *A61K 8/361* (2013.01); *A61K 8/81* (2013.01); *A61Q 1/00* (2013.01); *A61Q 1/02* (2013.01); *A61Q 5/00* (2013.01); *A61Q 17/04* (2013.01); *A61Q 19/00* (2013.01)

(58) Field of Classification Search
CPC .......... A61K 8/062; A61K 8/345; A61K 8/81; A61Q 1/02
See application file for complete search history.

(56) References Cited

U.S. PATENT DOCUMENTS

| | | | | |
|---|---|---|---|---|
| 2011/0070173 A1* | 3/2011 | Yoshida | ................. | A61K 8/06 424/59 |
| 2012/0156271 A1* | 6/2012 | Matsuzawa | ............. | A61K 8/03 424/401 |

FOREIGN PATENT DOCUMENTS

| | | | |
|---|---|---|---|
| JP | 59-139920 | A | 8/1984 |
| JP | 10-087427 | A | 4/1998 |
| JP | 2003238390 | * | 8/2003 |
| JP | 2004-231530 | A | 8/2004 |
| JP | 3614511 | B2 | 1/2005 |
| JP | 2007-314455 | A | 12/2007 |
| JP | 2008-088092 | A | 4/2008 |
| JP | 2008088092 | MT * | 4/2008 |
| JP | 2008-150299 | A | 7/2008 |
| JP | 2009-234996 | A | 10/2009 |
| JP | 2011-032249 | A | 2/2011 |
| JP | 2013-95698 | A | 5/2013 |
| JP | 2013-193999 | A | 9/2013 |
| WO | 2011/016363 | A1 | 2/2011 |
| WO | 2013/065643 | A1 | 5/2013 |

OTHER PUBLICATIONS

Title: Butylene glycol; product information downloaded from http://cosmetics.specialchem.com/inci/butylene-glycol/c-ingredients-thickeners-stabilizers#dvsearch.*
SkinCareRx, title: pH balance of skin, downloaded on Dec. 12, 2016.*
SAAPedia; titel: 2-Ethylhexyl p-methoxycinnamate, published Mar. 13, 2013. Downloaded from http://www.saapedia.org/en/saa/?type=detail&id=5660 Jun. 19, 2017.*
Yoshikazu Hirai, et al., "Characteristics and applications of fine o/w emulsions prepared by D-Phase Emulsification", Fragrance Journal, Apr. 15, 1993, pp. 34-41, vol. 21, No. 4, 111.
International Search Report of PCT/JP2014/062297, dated Aug. 5, 2014. [PCT/ISA/210].
Written Opinion of PCT/JP2014/062297, dated Aug. 5, 2014. [PCT/ISA/237].

* cited by examiner

*Primary Examiner* — Yanzhi Zhang
(74) *Attorney, Agent, or Firm* — Sughrue Mion, PLLC

(57) ABSTRACT

Provided is a cosmetic in the form of an oil-in-water emulsion unckuding (A) a salt of higher fatty acid component containing a liquid higher fatty acid and (B) an oil-soluble ultraviolet absorber, being substantially free of a hydrophilic surfactant other than the (A) component and having a pH of 7.1 to 9.5 and a method for production thereof. The cosmetic having ultraviolet protection efficacy is excellent in fresh feel, water resistance and rinsability using water with soap when applied to the skin and storage stability. The cosmetic is suitable for sunscreen cosmetics and is also useful for makeup cosmetics such as foundation and makeup base, skin care cosmetics such as milky lotion, cream and serum and hair cosmetics.

15 Claims, No Drawings

OIL-IN-WATER EMULSION COSMETIC AND METHOD FOR PRODUCING SAME

CROSS REFERENCE TO RELATED APPLICATIONS

This application is a National Stage of International Application No. PCT/JP2014/062297 filed May 8, 2014, claiming priority based on Japanese Patent Application No. 2013-101021, filed May 13, 2013, the contents of all of which are incorporated herein by reference in their entirety.

FIELD OF THE INVENTION

The present invention relates to a cosmetic in the form of an oil-in-water emulsion that is excellent in water resistance, as well as sunscreen efficacy, when applied to the skin and is excellent in rinsability. Also, the present invention relates to a method for producing the cosmetic.

BACKGROUND OF THE INVENTION

The adverse effects of ultraviolet rays have drawn attention in the recent years. Thus, various kinds of sunscreen cosmetics have been developed. For example, there are known sunscreen cosmetics having a form such as water-in-oil type, oil-in-water type and solvent type.

Among these, the sunscreen cosmetics of water-in-oil type or solvent type have generally good water resistance, since oil components or solvents contained in the composition make a continuous phase to form a cosmetic film with hydrophobicity when applied to the skin.

However, since these cosmetics sometimes provide a heavy greasy sensation and poor spreadability when applied to the skin, they are not suitable as a cosmetic to be used during the hot and humid midsummer when they are used with high frequency.

Further, these cosmetics have an inconvenience that the cosmetic film formed thereby is difficult to be completely removed without using a special make-up remover due to its hydrophobicity.

In contrast, sunscreen cosmetics in the form of an oil-in-water emulsion in which water makes a continuous phase are excellent in freshening texture and spreadability when applied to the skin. However, sunscreen cosmetics containing an oil-soluble ultraviolet absorber need a large amount of hydrophilic surfactant for dispersing the oil-soluble ultraviolet absorber. Therefore, such sunscreen cosmetics have a drawback that they are insufficient in durability as a cosmetic film due to their affinity for sweat and water. Thus, it has been eagerly desired to develop cosmetics in the form of an oil-in-water emulsion which retain the good freshening texture and have good durability as a cosmetic film, and various kinds of proposals concerning such cosmetics have been provided to date.

For example, Patent literature 1 discloses oil-in-water emulsion compositions containing a complex obtained by mixing an ampholytic surfactant and/or a semi-polar surfactant and a higher fatty acid, a powder, water and a non-volatile oil component. These oil-in-water emulsion compositions contain a liquid non-volatile oil component, such as dimethyl polysiloxane, to improve water resistance. These compositions raise a problem that the emulsions become unstable when a large amount of oil-soluble ultraviolet absorber with high polarity is incorporated to enhance ultraviolet protection efficacy. Also, the compositions are still insufficient in water resistance.

Further, Patent literature 2 proposes oil-in-water emulsion compositions containing a powder coated with a polymer composed of specified monomers having carboxyl groups and a basic compound both of which are dispersed in an aqueous phase. These cosmetic compositions are designed to make metal oxides, which are used as an agent for scattering ultraviolet rays, disperse stably in an aqueous phase and to improve water resistance. These cosmetic compositions differ in composition from emulsion compositions containing an oil-soluble ultraviolet absorber. Further, Patent literature 2 discloses that addition of a higher fatty acid is not preferable since the higher fatty acid neutralizes a basic compound so as to form a salt of higher fatty acid that significantly deteriorates water resistance (refer to paragraph [0038]).

Further, Patent literature 3 proposes oil-in-water emulsion cosmetics for sunscreen containing (A) a higher fatty acid, (B) a higher alcohol, (C) a glycerin derivative and (D) a ultraviolet absorber, being free of a hydrophilic surfactant, and having a pH of from 5.0 to 7.0. The Patent literature 3 discloses that oil-in-water emulsion cosmetics with good stability can be obtained without using a hydrophilic surfactant, and that the cosmetics have mild acidity, very weak irritation to the skin, high water resistance, good resistance for water and sweat and good durability of cosmetic film during the hot and humid midsummer and upon exercising (refer to paragraph [0034]). But, the Patent literature 3 discloses that these compositions need to contain the (A) higher fatty acid, the (B) higher alcohol and the (C) glycerin derivative in a specified proportion and that, where emulsion compositions are free of the (B) higher alcohol or the (C) glycerin derivative, stable emulsion compositions cannot be obtained due to insufficient emulsifying capacity (refer to comparative examples 1 and 2). Also, the Patent literature 3 discloses that emulsion compositions prepared by using the (A) higher fatty acid and a nonionic surfactant exhibit weak alkalinity, weak irritation to the skin and insufficient water resistance (refer to comparative example 7).

PRIOR ART REFERENCE

Patent Literature

Patent Literature 1: Japanese Laid-open Patent Publication No. 2004-231530
Patent Literature 2: Japanese Laid-open Patent Publication No. 2008-150299
Patent Literature 3: Japanese Patent Publication No. 3614511

DISCLOSURE OF THE INVENTION

Problem to be Solved by the Invention

The present invention has been achieved in view of such a background, and an object of the present invention is to provide an oil-in-water emulsion cosmetic that is excellent in storage stability of emulsions, water resistance when applied to the skin and easiness of rinsing off while keeping excellent feel in use peculiar to conventional oil-in-water emulsion cosmetics. Also, another object of the present invention is to provide a method for producing efficiently the oil-in-water emulsion cosmetics.

Means to Solve the Problem

The present inventors made extensive researches about a method for improving water resistance of an oil-in-water emulsion cosmetic comprising an oil-soluble ultraviolet absorber and found that, in the case that a salt of higher fatty acid component containing a liquid higher fatty acid is solely used as a surfactant for preparing an oil-in-water emulsion cosmetic and a pH of the composition is controlled within a specified range, it is possible to obtain an oil-in-water emulsion cosmetic with good storage stability that has little irritation, improved water resistance and excellent feel in use when applied to the skin, and can be easily rinsed off with soap. The present invention has been completed based on this finding.

Thus, first, the present invention provides a cosmetic in the form of an oil-in-water emulsion comprising from 0.5% to 12% by mass of (A) a salt of higher fatty acid component comprising a liquid higher fatty acid and from 2% to 30% by mass of (B) an oil-soluble ultraviolet absorber, wherein the cosmetic is substantially free of a hydrophilic surfactant other than the (A) salt of higher fatty acid component, and has a pH of 7.1 to 9.5.

Second, the present invention provides a method for producing the cosmetic comprising;
a step for preliminarily preparing an oil phase containing a higher fatty acid that is a raw material of the (A) salt of higher fatty acid component and the (B) oil-soluble ultraviolet absorber; and a step for adding an aqueous phase containing a basic compound that is a raw material of the (A) salt of higher fatty acid component to the resulting oil phase.

Third, the present invention provides a method for producing the cosmetic comprising;
a step for preliminarily preparing a D-phase containing the (A) salt of higher fatty acid component, (D) polyhydric alcohol and water;
a step for adding an oil phase containing the (B) oil-soluble ultraviolet absorber to the D-phase to form a gelled emulsion (O/D phase); and
a step for diluting the resulting gelled emulsion with water that is provided as necessary.

Effect of the Invention

The oil-in-water emulsion cosmetic of the present invention is excellent in freshening texture and is also excellent in water resistance and durability of ultraviolet ray barrier efficacy when applied to the skin, and is excellent in storage stability, and can be easily rinsed off with soap. Further, according to the present invention, the oil-in-water emulsion cosmetic having the foregoing benefits can be produced efficiently.

EMBODIMENT FOR CARRYING OUT THE INVENTION

Oil-In-Water Emulsion Cosmetic

The oil-in-water emulsion cosmetic of the present invention is composed of an emulsion comprising, relative to the entire amount of the cosmetic, 0.5% to 12% by mass of (A) a salt of higher fatty acid component containing a liquid higher fatty acid and 2% to 30% by mass of (B) an oil-soluble ultraviolet absorber, and is substantially free of a hydrophilic surfactant other than the (A) salt of higher fatty acid component, and has a pH of 7.1 to 9.5. In particular, preferred is an oil-in-water emulsion cosmetic that forms a cosmetic film exhibiting a pH of 7 or less, preferably 6.7 or less at the time after applied to human skin with a pH of 5.1 at a rate of 2 mg/cm$^2$.

In the present invention, the above mentioned (A) component, i.e., salt of higher fatty acid component containing a liquid higher fatty acid, is used as an emulsifier. The higher fatty acid component used for making the salt may be composed solely of a liquid higher fatty acid, and may also be composed of a mixture of a liquid higher fatty acid and a solid higher fatty acid. It is important for the higher fatty acid component to contain a liquid higher fatty acid. In the case that the higher fatty acid component is composed solely of a solid higher fatty acid, the resultant oil-in-water emulsion cosmetics become insufficient in spreadability when applied to the skin and become difficult to be rinsed off with soap.

The content of the liquid higher fatty acid ranges at least 30% by mass, preferably 50% or more by mass, further preferably 90% or more by mass relative to the entire amount of higher fatty acid component. With increase of the content, the resultant oil-in-water emulsion cosmetics become sufficient in spreadability when applied to the skin and become easy to be rinsed off with soap.

Further, where the higher fatty acid component is composed solely of a liquid higher fatty acid, there are benefits from an economical standpoint, as well as quality stability, because an oil-in-water emulsion can be prepared without a step for heating the higher fatty acid component.

The liquid higher fatty acid usually contains from 9 to 25 carbon atoms, preferably from 11 to 22 carbon atoms. Examples thereof include oleic acid, linoleic acid, linolenic acid, arachidonic acid, hexyl decanoic acid, isostearic acid and the like. These may be used solely or in combination of two or more compounds. Of these, isostearic acid, hexyl decanoic acid and oleic acid are preferred in view of function as an emulsifier, stability against oxidation and fresh feel. Specifically, isostearic acid is preferred.

In the present invention, the term "isostearic acid" means a branched stearic acid or a mixture of two or more branched stearic acids. For example, 5,7,7-trimethyl-2-(1,3,3-trimethylbutyl)-octanoic acid can be prepared by producing C9 branched aldehydes by oxo reaction of isobutylene dimer, subsequently producing C18 branched unsaturated aldehyde by aldol condensation of C9 branched aldehydes, and then subjecting the C18 branched unsaturated aldehyde to hydrogenation reaction and oxidation reaction in turn. Hereinafter, this type of isostearic acid is sometimes referred to "aldol condensation type". Isostearic acid of "aldol condensation type" is commercially available, for example, from Nissan Chemical Industries, Ltd.

Further, 2-heptyl undecanoic acid can be manufactured by oxidizing nonyl alcohol dimer which is obtained by subjecting nonyl alcohol to Guerbet reaction. This compound is commercially available from Mitsubishi Chemical Corporation and a similar compound having a small difference in branch-positions is commercially available from Nissan Chemical Industries, Ltd. Hereinafter, these compounds as a whole are sometimes referred to isostearic acid of "Guerbet reaction type".

Further, isostearic acid referred to "Emery type" can be used. Isostearic acid of "Emery type" means isostearic acid obtained by hydrogenating unsaturated fatty acids which are by-products in the reaction for synthesizing dimer acid from oleic acid, and having unknown structure, 18 carbon atoms and one or more methyl groups as a side chain (e.g. refer to J. Amer. Oil Chem. Soc. 51, 522 [1974]). Examples of such compounds include isostearic acid which was commercially available from Emery Oleochemicals and Isostearic Acid EX commercially available from Kokyu Alcohol Kogyo Co., Ltd. A starting material of dimer acid, which is a starting material for preparing isostearic acid of an "Emery type," is usually oleic acid, but may contain linoleic acid, linolenic acid, etc. In the present invention, the isostearic acid of an "Emery type" is particularly preferred.

In the present invention, the liquid fatty acid may be used in combination with a solid fatty acid which usually contains from 10 to 25, preferably from 11 to 22 of carbon atoms. Examples of the solid fatty acid include stearic acid, behenic acid, hydroxy stearic acid, palmitic acid, myristic acid, lauric acid, etc.

On the other hand, the basic compound constituting the above-mentioned (A) component is not limited as long as it is acceptable for preparing cosmetics, and examples of the basic compound include sodium hydroxide, potassium hydroxide, triethanolamine, etc.

The above-mentioned (A) component may be used in the form of a salt of the higher fatty acid preliminarily neutralized with a base, and may also be prepared during the production process of cosmetics by separately adding a higher fatty acid component and a basic compound to neutralize both components in situ.

In the latter method, the higher fatty acid component is usually added in an amount of the same equivalent as that of the basic compound. However, it is not necessary to use both components in an equal equivalent as long as the resultant emulsions exhibit a pH of 7.1 to 9.5. The molar ratio of the higher fatty acid component to the basic compound (i.e. higher fatty acid component/basic compound) may be appropriately selected within a range of 1/0.5 to 1/1.5.

The oil-in-water emulsion cosmetic of the present invention contains (A) component ranging from 0.5% to 12%, preferably 0.8% to 8%, more preferably 1% to 5% by mass relative to the entire amount of the cosmetic. It becomes difficult to obtain stable emulsions where the content of (A) component is less than 0.5% by mass, while water resistance of a cosmetic film formed on human skin deteriorates where the content of (A) component is more than 12% by mass.

In the present invention, it is important that the cosmetic is substantially free of a hydrophilic surfactant other than the above-mentioned (A) component. Examples of such a hydrophilic surfactant include anion surfactant other than the salt of the higher fatty acid, cationic surfactant, ampholytic surfactant and nonionic surfactant having a HLB of 7 or more.

The term "substantially free" means to exclude emulsions that contain these hydrophilic surfactants in an amount where they function as a surfactant and adversely affect water resistance of cosmetic film formed on the skin.

Specifically, in the case that these hydrophilic surfactants are present in the cosmetic, it is preferred that the content of these hydrophilic surfactants is 0.2% or less by mass, particularly 0.1% or less by mass relative to the entire amount of the cosmetic.

Further, it is preferred that no nonionic surfactant having a HLB of less than 7 is contained since it tends to deteriorate water resistance.

In the case that such a nonionic surfactant is present in the cosmetic, the content thereof is preferably 1.0% or less, more preferably 0.5% or less by mass relative to the entire amount of the cosmetic.

The oil-in-water emulsion cosmetic of the present invention has a pH ranging from 7.1 to 9.5, preferably from 7.2 to 8.5. It becomes difficult to obtain good emulsions where pH of the cosmetic is less than 7.1. In addition, the resulting emulsions are insufficient in storage stability and are apt to separate an oil phase from an aqueous phase immediately after they are prepared or during storage thereof.

On the other hand, where pH of the cosmetic is more than 9.5, water resistance becomes insufficient since a cosmetic film formed on human skin exhibits a pH of 7.0 or more.

Basically, pH of the cosmetic depends on a molar ratio of the higher fatty acid and the basic compound. In the case that the cosmetic contains any component affecting on pH other than the essential components specified in the present invention, it is adjusted so as to have a pH ranging from 7.1 to 9.5 by adding an appropriate amount of basic compound or a pH buffer as necessary.

Though there is no definite knowledge with respect to the mechanism of how water resistance is improved when the oil-in-water emulsion cosmetic of the present invention is applied to the skin, the present inventors speculate as follows.

That is, it is conventionally known that the skin surface exhibit a mild acidity with a pH of about 4.0 to about 6.4 (refer to Journal of Society of Cosmetic Chemists of Japan, Vol. 15, No. 2, p. 121-127, 1981 by Katsuhiko Deguchi et al. and Journal of Japan Oil Chemist's Society, Vol. 1, No. 2, p. 67-70, 1952 by Masao Nonaka).

Where the oil-in-water emulsion cosmetic of the present invention is applied to the surface of skin, a cosmetic film formed on the skin exhibits a pH of 7 or less, preferably 6.7 or less since the cosmetic is buffered by acid materials and the like existing on the skin surface.

When the pH of the cosmetic film becomes less than 7.0, the salt of the higher fatty acid contained therein loses the function of a surfactant because it changes from the fatty acid ion to the free fatty acid. As a result, the oily film formed on the skin surface becomes hard to be re-emulsified, and thereby water resistance is improved.

Accordingly, if the cosmetic has a pH of more than 9.5 or contains salts of the higher fatty acid in amount of more than 12% by mass, a cosmetic film with good water resistance becomes difficult to obtain since it becomes hard to form an oily film having a pH of 7.0 or less when the cosmetic is applied to the skin.

Further, this oily film can be easily re-emulsified since the higher fatty acid contained therein changes to the salt of the higher fatty acid in a basic environment. Therefore, the oily film becomes easily rinsed off using water with soap.

In the present invention, the pH of the skin surface applied with the cosmetic is measured by using pH meter (Skin Checker MJ-120, Sato Shoji Inc.) at the time of 30 minutes after the cosmetic is applied on the forearm in an amount of 2 mg/cm$^2$.

The oil-soluble ultraviolet absorber used as (B) component in the present invention is not particularly limited as long as it is acceptable for preparing cosmetics or external medicines for skin. The oil-soluble ultraviolet absorber may be used solely or in combination of two or more compounds. Examples of such an oil-soluble ultraviolet absorber include
ultraviolet absorbers of cinnamic acid type such as benzyl p-methoxycinnamate, 2-ethylhexyl p-methoxycinnamate, glyceryl mono-2-ethylhexanoate di-p-methoxycinnamate;
ultraviolet absorbers of benzophenone type such as hydroxy methoxybenzophenone, dihydroxy methoxybenzophenone, dihydroxybenzophenone, tetra-hydroxybenzophenone;
ultraviolet absorbers of benzoic acid ester type such as p-aminobenzoic acid, ethyl p-aminobenzoate, glyceryl p-aminobenzoate, amyl p-dimethylaminobenzoate, octyl p-dimethylaminobenzoate, ethyl 4-[N,N-di-(2-hydroxypropyl)amino]benzoate, diethylamino hydroxybenzoyl hexyl benzoate;

ultraviolet absorbers of salicylic acid type such as ethylene glycol salicylate, phenyl salicylate, octyl salicylate, benzyl salicylate, p-ter-butylphenyl salicylate, homomentyl salicylate;

ultraviolet absorbers of triazine type such as ethylhexyl triazone (2,4,6-tris [4-(2-ethyl hexyloxycarbonyl)anilino] 1,3,5-triazine), bis-ethylhexyloxyphenol methoxyphenyl triazine;

other ultraviolet absorbers such as 4-tert-butyl 4'-methoxy dibenzoylmethane, 5-methyl-2-isopropylcyclohexyl anthranilate, 2-(2-hydroxy-5-methylphenyl) benzotriazole, 2-ethylhexyl dimethoxybenzylidene dioxoimidazolidine propionate, octocrylene, dimethicodiethylbenzalmalonate.

Of these, 2-ethylhexyl p-methoxycinnamate, glyceryl mono-2-ethylhexanoate di-p-methoxycinnamate, octyl salicylate, homomentyl salicylate, bis-ethylhexyloxyphenol methoxyphenyl triazine, dihydroxybenzophenone, octocrylene, 4-tert-butyl 4'-methoxy dibenzoylmethane and diethylamino hydroxybenzoyl hexyl benzoate are particularly preferred in view of enhanced ultraviolet protection efficacy.

The oil-in-water emulsion cosmetic of the present invention contains (B) component of from 2% to 30%, preferably 5% to 25%, more preferably 8% to 22% by mass relative to the entire amount of the cosmetic.

The ultraviolet protection efficacy becomes insufficient when the content of (B) component is less than 2% by mass, while feel in use deteriorates and anxiety on irritation to the skin arises when the content of (B) component is more than 30% by mass.

The oil-in-water emulsion cosmetic of the present invention preferably contains (C) a water-soluble thickener in addition to the above mentioned (A) component and (B) component. The content of (C) component is usually from 0.01% to 3%, preferably from 0.05% to 2% by mass relative to the entire amount of the cosmetic. The addition of (C) component enables resultant compositions to have desired viscosity and feel in use, and more enhanced storage stability.

Examples of the water-soluble thickener include carboxy vinyl polymer, sodium polyacrylate, polyethylene glycol, acrylic acid-alkylmethacrylate copolymer, polyoxyethylene-polyoxypropylene block copolymer, polyvinyl alcohol, polyvinyl pyrrolidone, polyvinyl methyl ether, methylcellulose, ethyl cellulose, hydroxyethyl cellulose, hydroxypropylcellulose, hydroxypropyl methylcellulose, cationized cellulose, sodium alginate, alginic acid propylene glycol ester, guar gum, locust bean gum, carragheenan, xanthan gum, dextran, bentonite etc. Preferred examples include carboxy vinyl polymer, acrylic acid-alkylmethacrylate copolymer, polyvinyl alcohol and hydroxypropyl methylcellulose. The water-soluble thickener may be used solely or in combination of two or more compounds.

The oil-in-water emulsion cosmetic of the present invention preferably contains (D) polyhydric alcohol in addition to the above mentioned (A) component and (B) component. The content of (D) component is usually from 0.3% to 30%, preferably from 1% to 25% by mass relative to the entire amount of the cosmetic. The addition of (D) component enables the cosmetic to have desired moisture-retaining property and feel in use.

Further, when the cosmetic is prepared according to D-phase emulsification method mentioned later under the condition that the ratio by mass of (A) component to (D) component (i.e. (A) component/(D) component) is from 1/0.2 to 1/10, the cosmetic has more improved storage stability.

Examples of the polyhydric alcohol include sorbitol, xylitol, propylene glycol, dipro pyrene glycol, 1,3-butylene glycol, glycerin, diglycerin and polyethylene glycol. The polyhydric alcohol may be used solely or in combination of two or more compounds. Of these, preferred are 1,3-butylene glycol and glycerin. Glycerin is most preferable for D-phase emulsification method The oil-in-water emulsion cosmetic of the present invention may contain other components acceptable for preparation of conventional cosmetics. Examples of the components include water-soluble ultraviolet absorber, powder, oil, water-soluble polymer other than the (C) component, film-forming agent, alcohol, clay mineral, resin, moisturizer other than the (D) component, antiseptic, antibacterial agent, fragrance, salts, antioxidant, pH adjustor, chelating agent, freshner, anti-inflammatory agent, component for making beautiful skin, vitamins, amino acids, nucleic acid and clathrate compound.

Examples of the water-soluble ultraviolet absorber include hydroxy methoxybenzophenone sulfonic acid, sodium hydroxy methoxybenzophenone sulfonate, sodium dihydroxy methoxybenzophenone difulfonate and 2-phenylbenzimidazole-5-sulfonic acid.

The powder is used to adjust feel in use or to impart makeup efficacy and is not limited by the form thereof such as platy, spindle shape and needle; particle size; structure such as porous powder and non-porous powder as long as acceptable for preparation of conventional cosmetics. The powder may be inorganic powders, glittering powders, organic powders, colorants or composite powders.

Examples of the powder include inorganic powders such as titanium oxide, zinc oxide, zirconium oxide, cerium oxide, iron oxide, ferric ferrocyanide, ultramarine, silica, magnesium carbonate, calcium carbonate, aluminium hydroxide, chromium hydroxide, carbon black, aluminum silicate, magnesium silicate, magnesium aluminum silicate, mica, smectite, bentonite, kaolin, synthetic mica, synthetic sericite, sericite, talc, silicon carbide, barium sulfate, and boron nitride;

glittering powders such as bismuth oxychloride, titanated mica, iron oxide coated mica, iron oxide coated titanated mica and organic pigment coated titanated mica and aluminum powder;

organic powders such as magnesium stearate, zinc stearate, N-acyllysine, polystyrene, nylon, polymethylmethacrylate, polymethylsilsesquioxane powder and organic polysiloxane elastomer powder.

These powders may be coated with conventional surface treatment agents. Examples of the surface treatment agent include inorganic compounds such as alumina, silica and iron oxide, fluorine compound, silicone compound, phosphatide, phospholipid derivative, metallic soap, wax, surface active agent, fat and hydrocarbon. These powders may be used solely or in combination of two or more compounds.

Oil components are not limited by type such as animal oil, vegetable oil and synthetic oil or a property such as solid oil, half-solid oil, liquid oil and volatile oil as long as they are acceptable for preparing conventional cosmetics. Examples of the oil component include hydrocarbons, fats, waxes, hardened oils, ester oils, higher alcohols, silicone oils, fluoropolymer oils and lanolin derivatives.

More specifically, there are exemplified hydrocarbons such as liquid paraffin, alpha-olefin oligomer, squalane and vaseline;

fats such as olive oil, castor oil, mink oil and macadamia nut oil;

waxes such as beeswax, carnauba wax, candelilla wax and spermaceti;

esters such as jojoba oil, di-isobutyl adipate, 2-ethylhexyl adipate, di-2-heptylundecyl adipate, alkylene glycol monoisostearate, isocetyl isostearate, trimethylolpropane triisostearate, ethylene glycol di-2-ethyl hexanoate, cetyl 2-ethylhexanoate, neopentyl glycol di-2-ethyl hexanoate, trimethylolpropane tri-2-ethyl hexanoate, pentaerythritol tetra-2-ethyl hexanoate, cetyl octanoate, octyldodecyl ester gum, oleyl oleate, octyldodecyl oleate, decyl oleate, neopentyl glycol di-caprate, iscetyl stearate, butyl stearate, diisopropyl sebacate, di-2-ethylhexyl sebacate, cetyl lactate, myristyl lactate, isopropyl palmitate, 2-ethylhexyl palmitate, 2-hexyldecyl palmitate, 2-heptylundecyl palmitate, cholesteryl 12-hydroxystearate, fatty acid dipentaerythrityl ester, isopropyl myristate, 2-octyldodecyl myristate, 2-hexyldecyl myristate, myristyl myristate, hexyldecyl dimethyloctnoate, ethyl laurate, hexyl laurate, 2-octyldodecyl N-lauroyl-L-glutamate, diisostearyl malate, pentaerythrityl rosinate, glyceryl triisooctanoate, glyceryl triisostearate, glyceryl tripalmitate, glyceryl tri-2-ethylhexanoate, glyceryl monostearate, glyceryl di-2-heptylundecnoate, glyceryl trimristate and diglyceryl monostearate;

amino acid-based oils such as di(phytosteryl/2-octyldodecyl) N-lauroyl-L-glutamate, di(cholesteryl/behenyl/octyldodecyl) N-lauroyl-L-glutamate and di(cholesteryl/octyldodecyl) N-lauroyl-L-glutamate;

higher alcohols such as stearyl alcohol, cetyl alcohol, behenyl alcohol, lauryl alcohol, oleyl alcohol and isostearyl alcohol;

silicones such as dimethyl polysiloxane with low degree of polymerization, methyl phenyl polysiloxane, decamethyl cyclopentasiloxane, octamethyl cyclotetrasiloxane, alkoxy-modified polysiloxane and fluorine-modified silicone;

fluorinated oils such as perfluoropolyether;

lanolin derivatives such as lanolin, acetylated lanolin, isopropyl lanolate, lanolin alcohol oil gelling agents such as dextrin fatty acid ester, sucrose fatty acid ester, starch fatty acid ester and calcium stearate.

These oil components may be used solely or in combination of two or more compounds. When the oil component is blended, the total content of the oil component and the oil-soluble ultraviolet absorber used as the above (B) component is usually from 3% to 50%, preferably from 6% to 30%, more preferably 10% to 25% by mass relative to the entire amount of the cosmetic. The addition of the oil component sometimes leads to better moisture-retaining property and feel in use.

Method for Producing Oil-in-Water Emulsion Cosmetics

The oil-in-water emulsion cosmetic of the present invention can be prepared by making the above-mentioned (B) component disperse in water containing the above-mentioned (A) component as a surfactant. Methods for preparing the oil-in-water emulsion cosmetic are not specifically limited, and following methods are exemplified.

(1) Method for preparing the oil-in-water emulsion cosmetics by preliminarily preparing an aqueous phase containing the (A) component and an oil phase containing the (B) component, and then adding gradually the oil phase to the aqueous phase with agitation (2) Method for preparing the oil-in-water emulsion cosmetics by preliminarily preparing an oil phase containing a higher fatty acid component and the (B) component, and then adding gradually an aqueous phase containing an basic compound to the oil phase with agitation. In this method, the higher fatty acid component and the basic compound constituting the (A) component are separately added to different phases from each other. In general, this method has been referred to as a soap-emulsification method or a reactive-emulsification method.

(3) Method for preparing the oil-in-water emulsion cosmetics by preliminarily preparing a mixture containing the (A) component, polyhydric alcohol and water which is referred to D-phase or detergent phase, then adding gradually an oil phase containing the (B) component to the D-phase to form a gelled emulsion (i.e. O/D phase) with agitation, and then diluting the gelled emulsion if necessary. This method is referred to as a D-phase emulsification method in the present specification.

Of these, oil-in-water emulsion cosmetics obtained by the soap-emulsification method indicated as the above (2) exhibits better storage stability as compared with that obtained by the method indicated as the above (1) since fine emulsions can be formed with less energy due to formation of soap, which functions as an emulsifier, at an interface between oil and water. Further, the D-phase emulsification method is specifically preferred because it is capable of providing oil-in-water emulsion cosmetics having a fine particle and good stability, and being excellent in spreadability on the skin and fresh feel when applied to the skin. Glycerin is preferably used as a polyhydric alcohol in the D-phase emulsification method. The ratio by mass of the (A) component to polyhydric alcohol (i.e. (A) component/polyhydric alcohol) preferably ranges from 1/0.2 to 1/10 and the ratio by mass of the (A) component to water (i.e. (A) component/water) preferably ranges from 1/0.2 to 1/10.

The (A) component is preferably prepared by adding separately a higher fatty acid component and a basic compound, both of which are raw materials thereof, and then making a salt of the higher fatty acid component during the production process of the cosmetic emulsions in view of operability and quality stability. When a liquid higher fatty acid is used solely as a raw material of the higher fatty acid component of the (A) component, it makes it possible to omit the heating process for melting a solid higher fatty acid which is necessary when using the solid higher fatty acid. Therefore, using the liquid higher fatty acid is economically favorable and contributes to stabilization of quality.

The oil-in-water emulsion cosmetic of the present invention may be in any form such as cream, gel, milky lotion, thin milky liquid. The cosmetic can be used as a sunscreen cosmetic, and can also be used as other cosmetics having a property to shield against ultraviolet rays. Examples of other cosmetics include makeup cosmetics such as foundation and makeup base; skin care cosmetics such as milky lotion, cream and serum; and hair cosmetics.

EXAMPLE

Hereinafter, the present invention will be further explained with reference to specific examples. However, the present invention is not limited by these examples. The amount of each component is expressed in mass % unless otherwise specified.

Example 1

Sunscreen cosmetic having the composition shown in Table 1 was prepared according to the following production procedure. The thus-obtained sunscreen cosmetic had a pH of 7.9. Next, the sunscreen cosmetic was applied to the skin of female panelists with pH of 5.1 or plates composed of Bioskin (Beaulax Corp.) in an amount of 2 mg/cm$^2$ by a finger covered with a finger cot. Then, 30 minutes after application of the sunscreen cosmetic, the pH and contact angle of the applied surfaces were measured according to the following evaluation method. Table 2 shows the results.

TABLE1 1

| | Component | (%) |
|---|---|---|
| 1 | Purified water | 2.84 |
| 2 | Citric acid | 0.01 |
| 3 | Potassium hydroxide | 0.25 |
| 4 | Glycerin | 5.00 |
| 5 | Isostearic acid *1 | 1.50 |
| 6 | 2-ethylhexyl p-methoxycinnamate | 20.00 |
| 7 | Cyclopentasiloxane | 1.00 |
| 8 | Trimethylsiloxysilocate | 17.00 |
| 9 | Purified water | Balance |
| 10 | Phenoxyethanol | 0.50 |

*1: Isostearic Acid EX available from Kokyu Alcohol Kogyo Co., Ltd.

Production Procedure

Preparation of the Cosmetic According to D-Phase Emulsification Method
(1) D-phase (a) is prepared by mixing components 1 to 5.
(2) Oil phase (b) is prepared by mixing components 6 to 8.
(3) Aqueous phase (c) is prepared by mixing components 9 and 10.
(4) O/D phase (d), which is a gel-like emulsion, is prepared by mixing the oil phase (b) with the D-phase (a) little by little at room temperature.
(5) The cosmetic is prepared by mixing the aqueous phase (c) with the O/D phase (d).

Method for Measuring pH pH is measured by using pH meter (Skin Checker MJ-120, Sato Shoji Inc.)

Method for Measuring Contact Angle

Contact angle is measured based on photographed appearances of water droplet formed on surfaces coated with the cosmetic when water droplet is dropped calmly thereon.

TABLE 2

| Evaluation No. | Portion to be applied | pH at the time of 30 minutes after applied | Contact angle |
|---|---|---|---|
| 1 | Skin (Inner side of forearm) | 6.2 | 76° |
| 2 | Plate of Bioskin | 7.9 | 15° |

As shown in Table 2, the sunscreen cosmetic of the present invention exhibits mild acidity 30 minutes after applied to the skin and has water-repellent function due to greater contact angle. By contrast, when it is applied to the plate of Bioskin, it is still mildly alkaline and is inferior in water-repellent property due to smaller contact angle.

Examples 2 to 6 and Comparative Examples 1 to 3

Sunscreen cosmetics were prepared according to the formulation shown in Table 3 and the following production procedure 1 or 2. The thus-obtained sunscreen cosmetics were evaluated relative to pH after applied to the skin, water-repellent property, feel in use (freshening texture and refreshing sensation), rinsability using water with soap and storage stability according to the following evaluation method.

The sunscreen cosmetic in Example 3 was prepared according to the following production procedure 2 and those in other examples and comparative examples were prepared according to the following production procedure 1. Table 3 shows the results.

Production Procedure 1

Preparation of the Cosmetic According to D-Phase Emulsification Method
(1) D-phase (a) is prepared by mixing components 1 to 5.
(2) Oil phase (b) is prepared by mixing components 6 to 10.
(3) Aqueous phase (c) is prepared by mixing components 12 to 16.
(4) Aqueous phase (d) is prepared by mixing components 17 to 20.
(5) O/D phase (e), which is a gel-like emulsion, is prepared by mixing the oil phase (b) with the D-phase (a) little by little at room temperature.
(6) The cosmetic is prepared by adding the aqueous phase (c) and the aqueous phase (d) in turn after mixing component 11 with the O/D phase (e) little by little.

Production Procedure 2

Preparation of the Cosmetic According to Soap Emulsification Method
(1) Aqueous phase (a) is prepared by mixing components 1 to 4 and 11 to 16.
(2) Oil phase (b) is prepared by mixing components 5 to 10.
(3) Aqueous phase (c) is prepared by mixing components 17 to 20.
(4) Emulsion (e) is prepared by mixing the aqueous phase (a) with the oil phase (b) little by little at room temperature.
(5) The cosmetic is prepared by mixing the aqueous phase (c) with the emulsion (e) little by little.

<Evaluation Method 1: Evaluation of Water-Repellent Property>

In 20 female panelists, each test sample was applied to the inner side of forearm in an amount of 2 mg/cm$^2$ by finger covered with finger cot. Then, water droplet was dropped calmly on the applied surface at the time of 30 minutes after application. Water-repellent property was evaluated based on contact angle of water droplet formed on the applied surface according to the following criteria.
⊚: Contact angle is 75° or more
○: Contact angle ranges from 60° to 75°
Δ: Contact angle ranges from 20° to 60°
x: Contact angle is less than 20°

<Evaluation Method 2: Evaluation of Feel in Use (Freshening Texture and Refreshing Sensation)>

In 20 female panelists, each test sample was applied to the face and evaluated by the organoleptic test having the following criteria with respect to feel in use (freshening texture and refreshing sensation) after application.
⊚: 16 or more of 20 panelists reported that they had a freshening texture and a refreshing sensation
○: 11 to 15 of 20 panelists reported that they had a freshening texture and a refreshing sensation
Δ: 6 to 10 or less of 20 panelists reported that they had a freshening texture and a refreshing sensation x: 5 or less of 20 panelists reported that they had a freshening texture and a refreshing sensation <Evaluation Method 3: Evaluation of Rinsability>

Each test sample was applied according to the same way as in the above Evaluation method 2. Subsequently, the cosmetic film formed thereby was rinsed off using water with solid alkaline soap (Kao White commercially available from Kao Corporation) and evaluated by the organoleptic test having the following criteria with respect to easiness of removal thereof.

⊚: 16 or more of 20 panelists answered that the cosmetic film was easily washed away.
○: 11 to 15 of 20 panelists answered that the cosmetic film was easily washed away.
Δ: 6 to 10 of 20 panelists answered that the cosmetic film was easily washed away.
x: 5 or less of 20 panelists answered that the cosmetic film was easily washed away.

<Evaluation Method 4: Evaluation of Storage Stability>

Each test sample was stored in the constant-temperature chamber at 50° C. for 30 days, subsequently it was observed by the naked eye with regard to the separation of oil phase and aqueous phase. Storage stability was evaluated according to the following criteria.

○: There was no separation of oil phase and aqueous phase even after 30 days elapsed.
Δ: There was separation of oil phase and aqueous phase when 30 days elapsed.
x: There appeared separation of oil phase and aqueous phase immediately upon preparation of sunscreen cosmetic.

Data shown in Table 3 demonstrate that the sunscreen cosmetics of the present invention provide excellent results in any of water-repellency, feel in use (freshening texture and refreshing sensation), rinsability using water with soap and storage stability, and that water-repellency deteriorates with an increase of pH of the cosmetic.

In particular, the cosmetic prepared according to the D-phase emulsification method shown in Example 2 is superior in feel in use (freshening texture and refreshing sensation) and is finer in emulsified state as compared with the cosmetic of Example 3 that has the same composition and is prepared according to the soap emulsification method.

The cosmetic shown in Comparative example 2 which contains isostearic acid and potassium hydroxide used for preparing the (A) component in an excessively small amount could not be evaluated since separation of oil phase and aqueous phase appeared immediately after preparation thereof.

In contrast, the cosmetic shown in Comparative example 3 which contains isostearic acid and potassium hydroxide used for preparing (A) component in an excessively large amount exhibited poor water-repellency since cosmetic film formed thereby has higher pH when applied to the skin, and did not attain to the level of the cosmetics prepared by the D-phase emulsification method in connection with feel in use (freshening texture and refreshing sensation) (refer to Examples 2, 4 to 6).

Example 7 and Comparative Example 4

Sunscreen cosmetics were prepared according to the formulation shown in Table 4 and the following production

TABLE 3

| | Example 2 | Example 3 | Example 4 | Example 5 | Example 6 | Example 1 | Com. Example 2 | Com. Example 3 |
|---|---|---|---|---|---|---|---|---|
| Component (%) | | | | | | | | |
| 1 Purified water | 2.84 | 2.84 | 2.84 | 2.84 | 2.84 | 2.84 | 2.84 | 2.84 |
| 2 Citric acid | 0.01 | 0.01 | 0.01 | 0.01 | 0.01 | 0.01 | 0.01 | 0.01 |
| 3 Potassium hydroxide | 0.25 | 0.25 | 0.30 | 0.35 | 0.83 | 0.45 | 0.06 | 2.00 |
| 4 Glycerin | 5.00 | 5.00 | 5.00 | 5.00 | 5.00 | 5.00 | 5.00 | 5.00 |
| 5 Isostearic acid *1 | 1.50 | 1.50 | 1.50 | 1.50 | 5.00 | 1.50 | 0.40 | 12.00 |
| 6 2-ethylhexyl p-methoxycinnamate | 20.00 | 20.00 | 20.00 | 20.00 | 20.00 | 20.00 | 20.00 | 20.00 |
| 7 Cyclopentasiloxane | 1.00 | 1.00 | 1.00 | 1.00 | 1.00 | 1.00 | 1.00 | 1.00 |
| 8 Trimethylsiloxysilicate | 1.00 | 1.00 | 1.00 | 1.00 | 1.00 | 1.00 | 1.00 | 1.00 |
| 9 Tocopherol | 0.05 | 0.05 | 0.05 | 0.05 | 0.05 | 0.05 | 0.05 | 0.05 |
| 10 Glyceryl tri(2-ethylhexanoate) | 17.00 | 17.00 | 17.00 | 17.00 | 17.00 | 17.00 | 17.00 | 17.00 |
| 11 Purified water | 10.00 | 10.00 | 10.00 | 10.00 | 10.00 | 10.00 | 10.00 | 10.00 |
| 12 Purified water | Balance | Balance | Balance | Balance | Balance | Balance | Balance | Balance |
| 13 Pentylene glycol | 2.00 | 2.00 | 2.00 | 2.00 | 2.00 | 2.00 | 2.00 | 2.00 |
| 14 Tetrasodium etidronate | 0.08 | 0.08 | 0.08 | 0.08 | 0.08 | 0.08 | 0.08 | 0.08 |
| 15 Xanthan gum | 0.20 | 0.20 | 0.20 | 0.20 | 0.20 | 0.20 | 0.20 | 0.20 |
| 16 Dipropylene glycol | 1.00 | 1.00 | 1.00 | 1.00 | 1.00 | 1.00 | 1.00 | 1.00 |
| 17 Potassium hydroxide | 0.10 | 0.10 | 0.10 | 0.10 | 0.10 | 0.10 | 0.10 | 0.10 |
| 18 Carboxyvinyl polymer | 0.40 | 0.40 | 0.40 | 0.40 | 0.40 | 0.40 | 0.40 | 0.40 |
| 19 Purified water | 19.60 | 19.60 | 19.60 | 19.60 | 19.60 | 19.60 | 19.60 | 19.60 |
| 20 Phenoxyethanol | 0.50 | 0.50 | 0.50 | 0.50 | 0.50 | 0.50 | 0.50 | 0.50 |
| Total | 100.00 | 100.00 | 100.00 | 100.00 | 100.00 | 100.00 | 100.00 | 100.00 |
| pH | 7.9 | 7.9 | 8.5 | 9.0 | 8.3 | 10.8 | — | 7.9 |
| Result of evaluation | | | | | | | | |
| pH of applied surface | 6.2 | 6.2 | 6.7 | 6.9 | 6.5 | 8.0 | — | 7.1 |
| Water-repellent property | ⊚ | ⊚ | ○ | ○ | ○ | X | — | Δ |
| Feel in use (freshening texture, refreshing sensation) | ⊚ | ○ | ⊚ | ⊚ | ⊚ | ⊚ | — | ○ |
| Rinsability | ⊚ | ⊚ | ⊚ | ⊚ | ⊚ | ⊚ | — | ⊚ |
| Storage stability | ○ | ○ | ○ | ○ | ○ | ○ | X | ○ | procedure. The thus-obtained sunscreen cosmetics were evaluated according to the same way as in Example 2. Table 4 shows the results.

Production Procedure

Preparation of the cosmetic according to D-phase emulsification method
(1) D-phase (a) is prepared by mixing components 1 to 7.
(2) Oil phase (b) is prepared by mixing components 8 to 12.
(3) Aqueous phase (c) is prepared by mixing components 14 to 18.
(4) Aqueous phase (d) is prepared by mixing components 19 to 22.
(5) O/D phase (e), which is a gel-like emulsion, is prepared by mixing the oil phase (b) with the D-phase (a) little by little at room temperature.
(6) The cosmetic is prepared by adding the aqueous phase (c) and the aqueous phase (d) in turn after mixing component 13 with the O/D phase (e) little by little.

TABLE 4

| | Component (%) | Example 7 | Com. Example 4 |
|---|---|---|---|
| 1 | Purified water | 2.84 | 2.84 |
| 2 | Citric acid | 0.01 | 0.01 |
| 3 | Potassium hydroxide | 0.25 | 0.25 |
| 4 | Glycerin | 5.00 | 5.00 |
| 5 | Isostearic acid *1 | — | 1.50 |
| 6 | Oleic acid | 1.50 | — |
| 7 | Glyceryl isostearate (PEG20) | — | 0.30 |
| 8 | 2-ethylhexyl p-methoxycinnamate | 20.00 | 20.00 |
| 9 | Cyclopentasiloxane | 1.00 | 1.00 |
| 10 | Trimethysiloxysilocate | 1.00 | 1.00 |
| 11 | Tocopherol | 0.05 | 0.05 |
| 12 | Glyceryl tri(2-ethylhexanoate) | 17.00 | 17.00 |
| 13 | Purified water | 10.00 | 10.00 |
| 14 | Purified water | Balance | Balance |
| 15 | Pentylene glycol | 2.00 | 2.00 |
| 16 | Tetrasodium etidronate | 0.08 | 0.08 |
| 17 | Xanthan gum | 0.20 | 0.20 |
| 18 | Dipropylene glycol | 1.00 | 1.00 |
| 19 | Potassium hydroxide | 0.10 | 0.10 |
| 20 | Carboxyvinyl polymer | 0.40 | 0.40 |
| 21 | Purified water | 19.60 | 19.60 |
| 22 | Phenoxyethanol | 0.50 | 0.50 |
| | Carboxyvinyl polymer | 100.00 | 100.00 |
| | pH | 7.9 | 7.9 |
| | Result of evaluation | | |
| | pH of applied surface | 6.2 | 6.2 |
| | Water-repellent property | ◎ | Δ |
| | Feel in use (freshening texture, refreshing sensation) | ◎ | ◎ |
| | Rinsability | ◎ | ◎ |
| | Storage stability | ○ | ○ |

Data shown in Table 4 demonstrate that the sunscreen cosmetics shown in Example 7 using oleic acid as the higher fatty acid exhibited almost the same properties as those of the cosmetic shown in Example 2 using the same amount of isostearic acid. In contrast, the cosmetic shown in Comparative example 4 using isostearic acid as the higher fatty acid and PEG-20 glyceryl isostearate with HLB of 12 as a nonionic surfactant was inferior in water-repellency despite having a pH of 7.9.

Comparative Example 5

The sunscreen cosmetic was prepared according to the formulation shown in Table 5 and the following production procedure. The thus-obtained sunscreen cosmetic was excellent in water-repellency and storage stability because of water-in-oil emulsion (W/O type), while it was insufficient in feel in use (freshening texture and refreshing sensation) and rinsability upon rinsing cosmetic film off using water with soap.

Production Procedure (1) Oil phase (a) is prepared by mixing components 1 to 7.
(2) Aqueous phase (b) is prepared by mixing components 8 to 11.
(3) The cosmetic is prepared by mixing the aqueous phase (b) with the oil phase (a) little by little at room temperature.

TABLE 5

| | Component (%) | (%) |
|---|---|---|
| 1 | 2-ethylhexyl p-methoxycinnamate | 10.00 |
| 2 | Cyclopentasiloxane | Balance |
| 3 | Trimethylsiloxysilicate | 1.00 |
| 4 | Tocopherol | 0.05 |
| 5 | Glyceryl tri(2-ethylhexanoate) | 17.00 |
| 6 | PEG-10 dimethicone | 4.00 |
| 7 | Disteardimonium hectorite | 1.00 |
| 8 | Purified water | 30.00 |
| 9 | Pentylene glycol | 2.00 |
| 10 | 1,3-butylene glycol | 2.00 |
| 11 | Phenoxyethanol | 0.50 |

Example 8

The sunscreen cosmetic containing isostearic acid as a liquid higher fatty acid and stearic acid as a solid higher fatty acid was prepared according to the formulation shown in Table 6 and the following production procedure. The thus-obtained sunscreen cosmetic was evaluated according to the same way as in Example 2. Table 6 shows the results.

Production Procedure

Preparation of the cosmetic according to the soap emulsification method
(1) Aqueous phase (a) is prepared, subsequent to mixing of components 1 to 9, by heating the mixture at 80 degree C.
(2) Oil phase (b) is prepared, subsequent to mixing of components 10 to 18, by heating the mixture at 80 degree C.
(3) Emulsion phase (c) is prepared by mixing the aqueous phase (a) with the oil phase (b) little by little.
(4) The cosmetic is prepared by mixing component 19 with the emulsion phase (c) at 35° C. after cooling the emulsion phase (c).

TABLE 6

| | Component (%) | (%) |
|---|---|---|
| 1 | Purified water | Balance |
| 2 | Citric acid | 0.01 |
| 3 | Potassium hydroxide | 0.35 |
| 4 | Glycerin | 5.00 |
| 5 | Carboxyvinyl polymer | 0.40 |
| 6 | Pentylene glycol | 2.00 |
| 7 | Tetrasodium etidronate | 0.08 |
| 8 | Xanthan gum | 0.20 |

TABLE 6-continued

| | | (%) |
|---|---|---|
| 9 | Dipropylene glycol | 1.00 |
| 10 | 2-ethylhexyl p-methoxycinnamate | 10.00 |
| 11 | Isostearic acid *1 | 1.50 |
| 12 | Stearic acid | 0.50 |
| 13 | Cyclopentasiloxane | 1.00 |
| 14 | Triethylsiloxysilicate | 1.00 |
| 15 | Tocopherol | 0.05 |
| 16 | Glyceryl tri(2-ethylhexanoate) | 17.00 |
| 17 | Cetanol | 0.20 |
| 18 | Glyceryl monostearate | 0.40 |
| 19 | Phenoxyethanol | 0.50 |
| | Total | 100.00 |
| | pH | 7.5 |
| | Result of evaluation | |
| | pH of applied surface | 6.0 |
| | Water-repellent property | ◎ |
| | Feel in use (freshening texture, refreshing sensation) | ○ |
| | Rinsability | ○ |
| | Storage stability | ○ |

Data shown in Table 6 demonstrate that the sunscreen cosmetic containing potassium isostearate and potassium stearate together also exhibited excellent properties.

Example 9

A makeup base cosmetic having a sunscreen function was prepared according to the formulation shown in Table 7 and the following production procedure. The thus-obtained makeup base cosmetic was evaluated according to the same way as in Example 2. Table 7 shows the results.

Production Procedure

Preparation of the cosmetic according to D-phase emulsification method
(1) D-phase (a) is prepared by mixing components 1 to 5.
(2) Oil phase (b) is prepared by mixing components 6 to 10.
(3) Aqueous phase (c) is prepared by mixing components 12 to 19.
(4) Aqueous phase (d) is prepared by mixing components 20 to 23.
(5) O/D phase (e), which is a gel-like emulsion, is prepared by mixing the oil phase (b) with the D-phase (a) little by little at room temperature.
(6) The cosmetic is prepared by mixing component 11 with the O/D phase (e) little by little, and then adding to the resultant mixture the aqueous phase (c) and the aqueous phase (d) in turn.

TABLE 7

| | Component (%) | (%) |
|---|---|---|
| 1 | Purified water | 2.75 |
| 2 | Citric acid | 0.01 |
| 3 | Potassium hydroxide | 0.25 |
| 4 | Glycerin | 5.00 |
| 5 | Isostearic acid*1 | 2.00 |
| 6 | 2-ethylhexyl p-methoxycinnamate | 10.00 |
| 7 | Cyclopentasiloxane | 10.00 |
| 8 | Trimethylsiloxysilicate | 1.00 |
| 9 | Tocopherol | 0.05 |
| 10 | Glyceryl tri(2-ethylhexanoate) | 17.00 |

TABLE 7-continued

| | | (%) |
|---|---|---|
| 11 | Purified water | 10.00 |
| 12 | Purified water | Balance |
| 13 | Pentylene glycol | 2.00 |
| 14 | Tetrasodium etidronate | 0.08 |
| 15 | Xanthan gum | 0.20 |
| 16 | Microcrystalline cellulose | 0.50 |
| 17 | Iron oxide coated with silica *2 | 0.05 |
| 18 | Yellow Oxide of Iron coated woth silica *3 | 0.15 |
| 19 | Dipropylene glycol | 1.00 |
| 20 | Carboxyvinyl polymer | 0.40 |
| 21 | Potassium hydroxide | 0.10 |
| 22 | Phenoxyethanol | 0.50 |
| | Total | 100.00 |
| | pH | 7.6 |
| | Result of evaluation | |
| | pH of applied surface | 6.1 |
| | Water-repellent property | ◎ |
| | Feel in use (freshening texture, refreshing sensation) | ◎ |
| | Rinsability | ◎ |
| | Storage stability | ○ |

*2: SYMPHOLIGHT RW (JGC Catalysts and Chemicals Ltd.)
*3: SYMPHOLIGHT Y10 (JGC Catalysts and Chemicals Ltd.)

Data shown in Table 7 demonstrate that the oil-in-water emulsion cosmetic was excellent in water-repellency, feel in use (freshening texture and refreshing sensation), rinsability by cleansing with soap and storage stability, even when it is used as a makeup base cosmetic.

INDUSTRIAL APPLICABILITY

The oil-in-water emulsion cosmetic of the present invention is excellent in fresh feel in use and water resistance when applied to the skin. In addition, it is excellent in durability of ultraviolet protection efficacy and storage stability. Further, it can be easily removed by cleansing with soap.

The oil-in-water emulsion cosmetic is suitable for a sunscreen cosmetic and is also useful for makeup cosmetics such as foundation and makeup base, skin care cosmetics such as milky lotion, cream and serum and hair cosmetics.

What is claimed is:
1. A cosmetic in the form of an oil-in-water emulsion comprising:
from 0.5% to 12% by mass of (A) a salt of fatty acid component, wherein the fatty acid component is composed of 75% to 100% by mass of a liquid higher fatty acid containing carbon atoms of from 9 to 25 and 0% to 25% by mass of a solid higher fatty acid containing carbon atoms of from 10 to 25 relative to the entire amount of the fatty acid component,
2% to 30% by mass of (B) an oil-soluble ultraviolet absorber relative to the entire amount of the cosmetic,
0.01% to 3% by mass of (C) a water-soluble thickener relative to the entire amount of the cosmetic, and
from 0.3% to 30% by mass of (D) a polyhydric alcohol relative to the entire amount of the cosmetic, and
no more than 0.2% by mass of a hydrophilic surfactant other than the (A) salt of fatty acid component relative to the entire amount of the cosmetic,
wherein the hydrophilic surfactant is an anion surfactant other than the (A) salt of fatty acid component, a cationic surfactant, an ampholytic surfactant or a nonionic surfactant having a HLB of 7 or more, the (A) salt of higher fatty acid component is sodium salt, potassium salt or triethanolamine salt, the liquid fatty acid is at least one selected from the group of oleic acid, linoleic acid, linolenic acid, arachidonic acid, hexyl decanoic acid and isostearic acid, and wherein the cosmetic has a pH of 7.1 to 9.5.

2. The cosmetic according to claim 1, wherein the cosmetic further comprises from 0.05% to 2% by mass of (C) a water-soluble thickener relative to the entire amount of the cosmetic.

3. The cosmetic according to claim 1, wherein the content of (A) salt of fatty acid component ranges from 0.8% to 8% by mass relative to the entire amount of the cosmetic.

4. The cosmetic according to claim 1, wherein the content of (B) oil-soluble ultraviolet absorber ranges from 5% to 25% by mass relative to the entire amount of the cosmetic.

5. The cosmetic according to claim 1, wherein the (A) salt of fatty acid component contains at least 90% by mass of the liquid higher fatty acid relative to the entire amount of the fatty acid component.

6. The cosmetic according to claim 5, wherein the (A) salt of fatty acid component composed solely of the liquid higher fatty acid.

7. The cosmetic according to claim 1, wherein the content of the hydrophilic surfactant other than (A) the salt of fatty acid component is no more than 0.1% by mass relative to the entire amount of the cosmetic.

8. The cosmetic according to claim 1, wherein the cosmetic exhibits a pH of 7 or less when it is applied to the human skin.

9. The cosmetic according to claim 1, wherein the cosmetic is prepared by soap emulsification method.

10. The cosmetic according to claim 1, wherein the cosmetic is prepared by D-phase emulsification method.

11. The cosmetic according to claim 1, wherein the cosmetic is a sunscreen cosmetic, makeup cosmetic, skin care cosmetic or hair cosmetic.

12. The cosmetic according to claim 1, wherein the water-soluble thickener is at least one selected from the group consisting of carboxy vinyl polymer, acrylic acid-alkylmethacrylate copolymer, polyvinyl alcohol, hydroxypropyl methylcellulose and xanthan gum.

13. The cosmetic according to claim 1, wherein the ratio by mass of (A) the salt of fatty acid component to (D) the polyhydric alcohol is from 1/0.2 to 1/10.

14. A method for producing the cosmetic according to claim 1, comprising;

a step for preliminarily preparing an oil phase containing a higher fatty acid having 9 to 25 carbon atoms which is a raw material of the (A) salt of fatty acid component and the (B) oil-soluble ultraviolet absorber; and a step for adding an aqueous phase containing a basic compound which is a raw material of the (A) salt of fatty acid component to the oil phase.

15. A method for producing the cosmetic according to claim 1, comprising;

a step for preliminarily preparing a D-phase containing the (A) salt of fatty acid component, the (D) polyhydric alcohol and water;

a step for adding an oil phase containing the (B) oil-soluble ultraviolet absorber to form a gelled emulsion; and optionally a step for diluting the gelled emulsion with water.

\* \* \* \* \*